(12) United States Patent
Bryant et al.

(10) Patent No.: US 7,192,693 B2
(45) Date of Patent: Mar. 20, 2007

(54) METHODS FOR PHOTOPATTERNING HYDROGELS

(75) Inventors: Stephanie J. Bryant, Shoreline, WA (US); Kip D. Hauch, Lynnwood, WA (US); Buddy D. Ratner, Seattle, WA (US)

(73) Assignee: University of Washington, Seattle, WA (US)

( * ) Notice: Subject to any disclaimer, the term of this patent is extended or adjusted under 35 U.S.C. 154(b) by 164 days.

(21) Appl. No.: 11/067,480

(22) Filed: Feb. 24, 2005

(65) Prior Publication Data

US 2005/0196702 A1 Sep. 8, 2005

Related U.S. Application Data

(60) Provisional application No. 60/547,127, filed on Feb. 24, 2004.

(51) Int. Cl.
*G03F 7/20* (2006.01)
*G03F 7/028* (2006.01)
*A61F 2/02* (2006.01)
*A61K 9/58* (2006.01)

(52) U.S. Cl. .................. 430/322; 430/288.1; 430/325; 430/396; 430/927; 424/78.31; 424/426; 424/487

(58) Field of Classification Search ............. 430/288.1, 430/322, 325, 396, 927; 424/78.31, 426, 424/487
See application file for complete search history.

(56) References Cited

U.S. PATENT DOCUMENTS 5,626,863 A * 5/1997 Hubbell et al. ............. 424/426
5,780,208 A * 7/1998 Ziger et al. ................. 430/394
6,537,569 B2 * 3/2003 Cruise ........................ 424/426

FOREIGN PATENT DOCUMENTS

WO  WO 2005/032418 A2  4/2005

OTHER PUBLICATIONS

Andrezejewska, Ewa, "Photopolymerization Kinetics of Multifunctional Monomers," *Progress in Polymer Science* 26:605-665, 2001.

Beebe, D.J, et al., "Functional Hydrogel Structures for Autonomous Flow Control Inside Microfluidic Channels," *Nature* 404:588-590, Apr. 6, 2000.

(Continued)

*Primary Examiner*—Richard L. Schilling
(74) *Attorney, Agent, or Firm*—Christensen O'Connor Johnson Kindness PLLC

(57) ABSTRACT

In one aspect, the invention provides methods for forming a photopatterned hydrogel. In some embodiments, the methods comprise the step of exposing a solution comprising a monomer, a crosslinking agent, and a photoinitiator to a pattern of light comprising a first and a second light intensity for a period of time and under suitable conditions for the first light intensity to induce essentially complete conversion of polymerizable groups on the monomer and the crosslinking agent to form a patterned hydrogel, and for the second light intensity to induce partial conversion of the polymerizable groups on the monomer and the crosslinking agent to form partially polymerized polymers that remain soluble. In some embodiments, the first light intensity is lower than the second light intensity. In another aspect, the invention provides methods for forming porous, photopatterned hydrogels.

23 Claims, 4 Drawing Sheets

OTHER PUBLICATIONS

Beebe, D.J, et al., "Physics and Applications of Microfluidics in Biology," *Annual Revue Biomedical Engineering* 4:261-286, 2002.

Chen, C., et al., "Gray-Scale Photolithography Using Microfluidic Photomasks," *PNAS* 100(4):1499-1504, Feb. 18, 2003.

Khoury, C., et al., "Ultra Rapid Protoyping of Microfluidic Systems Using Liquid Phase Photopolymerization," *Lab Chip* 2:50-55, 2002.

Koh, W-G., et al., "Poly(ethylene glycol) Hydrogel Microstructures Encapsulating Living Cells," *Langmuir* 18:2459-2462, 2002.

Liu, V.A., and S.N. Bhatia, "Three-Dimensional Photopatterning of Hydrogels Containing Living Cells," *Biomedical Microdevices* 4(4):257-266, 2002.

Revzin, A., et al., "Surface Engineering with Poly(ethylene glycol) Photolithography to Create High-Density Cell Arrays on Glass," *Langmuir* 19:9855-9862, 2003.

Snyder, J.D., and T.A. Desai, "Microscale Three-Dimensional Polymeric Platforms for *In Vitro* Cell Culture Systems," *J. Biomater. Sci. Polymer Edn.* 12(8):921-932, 2001.

\* cited by examiner

METHODS FOR PHOTOPATTERNING HYDROGELS

CROSS-REFERENCE TO RELATED APPLICATION

This application claims the benefit of U.S. Provisional Application No. 60/547,127, filed Feb. 24, 2004, under 35 U.S.C. § 119.

STATEMENT OF GOVERNMENT LICENSE RIGHTS

The U.S. Government has a paid-up license in this invention and the right in limited circumstances to require the patent owner to license others on reasonable terms as provided for by the terms of Grant Nos. R24HL64387 and F32HL74619 awarded by the National Institutes of Health.

FIELD OF THE INVENTION

The present invention relates to methods for forming photopatterned hydrogels and methods for forming photopatterned porous hydrogel scaffolds for tissue engineering.

BACKGROUND OF THE INVENTION

By existing methods, photopatterning of liquid phase polymerizations occurs using a photomask where a pattern is defined by the clear and dark regions. The initiating light penetrates through the clear region of the mask, exposes the underlying solution, and initiates the polymerization reaction. The dark regions block the initiating light and prevent the polymerization reaction. Patterned hydrogels have been fabricated using photopolymerization reactions in combination with a photomask to create 3-D structures. For example, photopatterning has been used to form patterned hydrogels from liquid phase polymerizations with thickness up to 180 micrometers and a resolution down to 25 micrometers (Beebe et al. (2000) *Nature* 404:588–90). Photopatterning has emerged as a simple, inexpensive technique that can be performed in standard laboratories to pattern channels for microfluidics (Khoury et al. (2002) *Lab on a Chip* 2:50–5) or cells in 3-D gels for tissue engineering (Snyder & Desai (2001) *J. Biomater. Sci. Poly. Ed.* 12:921–32; Liu & Bhatia (2002) *Biomed. Microdev.* 4:257–66; Koh et al. (2002) *Langmuir* 18:2459–62). However, the limitations of patterning from liquid phase solutions using photolithography techniques include limited pattern depth and resolution.

Recently, the fabrication of a well-defined porous material has been reported using indirect solid free-form fabrication (iSSF). This technique uses a computational design of a 3D structure that is printed layer-by-layer using specially designed printing equipment to form a 3D structure (e.g., that is made out of wax). A polymer solution (e.g., poly(lactic acid) containing salt as a poragen forming species) is then cast onto the 3D structure. Upon removing the wax and leaching out the salt, a porous scaffold with a well-defined macro-architecture is generated. This approach to patterning porous materials is expensive and requires specialized equipment.

Thus, there is a need for methods for photopatterning hydrogels and for making porous hydrogel scaffolds that overcome the disadvantages of prior art methods.

SUMMARY OF THE INVENTION

In one aspect, the invention provides methods for forming a photopatterned hydrogel. In some embodiments, the methods comprise the step of exposing a solution comprising a monomer, a crosslinking agent, and a photoinitiator to a pattern of light comprising a first and a second light intensity for a period of time and under suitable conditions for the first light intensity to induce essentially complete conversion of polymerizable groups on the monomer and the crosslinking agent to form a patterned hydrogel, and for the second light intensity to induce partial conversion of the polymerizable groups on the monomer and the crosslinking agent to form partially polymerized polymers that remain soluble. In some embodiments, the first light intensity is lower than the second light intensity.

The polymerizable group on the monomer and crosslinking agent may be a methacrylate or an acrylate group. Exemplary monomers that may be used in the methods include, but are not limited to, methacrylates derivatives, acrylate derivatives, ethylene, dienes, styrenes, halogenated olefins, vinyl esters, acrylonitriles, acrylamides, n-vinyl pyrrolidones, and mixtures thereof. Suitable methacrylate derivatives include, but are not limited to, 2-hydroxyethyl methacrylate, methyl methacrylate, methacrylic acid, n-butyl methacrylate, glycidyl methacrylate, n-propyl methacrylate, poly(ethylene glycol) monomethacrylate, and mixtures thereof. Suitable acrylate derivatives include, but are not limited to, 2-hydroxyethyl acrylate, 2-methoxyethyl acrylate, acrylic acid, n-butyl acrylate, glycidyl acrylate, n-propyl acrylate, poly(ethylene glycol) monoacrylate, and mixtures thereof.

Exemplary crosslinking agents that may be used in the methods include, but are not limited to, tetraethylene glycol dimethacrylate, tetraethylene glycol diacrylate, ethylene glycol dimethacrylate, ethylene glycol diacrylate, dipropylene glycol dimethacrylate, dipropylene glycol diacrylate, poly(ethylene glycol)dimethacrylate, poly(ethylene glycol) diacrylate, bisacrylamide, and mixtures thereof.

Exemplary photoinitiators that may be used in the methods include 2,2-dimethoxy acetophenone, 1-hydroxycyclohexyl phenyl ketone, 2-methyl-1-[4-(methylthio)phenyl]-2-(4-morpholinyl)-1-propoanone, 2-hydroxy-1-[4-(hydroxyethoxy)phenyl]-2-methyl-1-propanone, and mixtures thereof.

Some embodiments provide methods for forming a degradable, photopatterned hydrogel. Suitable crosslinking agents for forming degradable, photopatterned hydrogels include hydrolytically degradable crosslinking agents and enzymatically degradable crosslinking agents. Exemplary degradable crosslinking agents include, but are not limited to, poly($\epsilon$-caprolactone)-b-tetraethylene glycol-b-poly($\epsilon$-caprolactone)dimethacrylate, poly($\epsilon$-caprolactone)-b-poly (ethylene glycol)-b-poly($\epsilon$-caprolactone)dimethacrylate, poly(lactic acid)-b-tetraethylene glycol-b-poly(lactic acid) dimethacrylate, poly(lactic acid)-b-poly(ethylene glycol)-b-poly(lactic acid)dimethacrylate, poly(glycolic acid)-b-tetraethylene glycol-b-poly(glycolic acid)dimethacrylate, poly (glycolic acid)-b-poly(ethylene glycol)-b-poly(glycolic acid)dimethacrylate, poly($\epsilon$-caprolactone)-b-tetraethylene glycol-b-poly($\epsilon$-caprolactone)diacrylate, poly($\epsilon$-caprolactone)-b-poly(ethylene glycol)-b-poly($\epsilon$-caprolactone)diacrylate, poly(lactic acid)-b-tetraethylene glycol-b-poly(lactic acid)diacrylate, poly(lactic acid)-b-poly(ethylene glycol)-b-poly(lactic acid)diacrylate, poly(glycolic acid)-b-tetraethylene glycol-b-poly(glycolic acid) diacrylate, poly (glycolic acid)-b-poly(ethylene glycol)-b-poly(glycolic acid) diacrylate, and mixtures thereof.

In some embodiments, the methods provide photopatterned hydrogels having a thickness greater than about 25 micrometers, such as a thickness between about 50 micrometers and about 1200 micrometers, or between about 100 micrometers and about 800 micrometers.

Some embodiments of the methods for forming a photopatterned hydrogel comprise the step of exposing a solution comprising a monomer, a cross-linking agent, and a photoinitiator to a pattern of light comprising a first and a second light intensity for a period of time under suitable conditions to form a photopatterned hydrogel defined by regions of the solution exposed to the first light intensity, wherein the first light intensity is lower than the second light intensity.

Another aspect of the invention provides methods for forming porous, photopatterned hydrogels. In some embodiments, the methods comprise the steps of: (a) exposing a plurality of porogens in a solution comprising a monomer, a crosslinking agent, and a photoinitiator to a pattern of light comprising a first and a second light intensity for a period of time under suitable conditions or the first light intensity to induce essentially complete conversion of polymerizable groups on the monomer and the crosslinking agent to form a patterned hydrogel, and for the second light intensity to induce partial conversion of polymerizable groups on the monomer and the crosslinking agent to form polymers that remain soluble; and (b) removing the plurality of porogens to form a porous, photopatterned hydrogel. In some embodiments, the first light intensity is lower than the second light intensity. Suitable monomers, crosslinking agents, and photoinitiators for use in this aspect of the invention include those used in the methods for making photopatterned hydrogels described above. Suitable porogens include, but are not limited to, beads (such as PMMA beads or polystyrene beads), salts, sugars, and waxes. The pore sizes of the porous patterned hydrogels may be varied simply through the choice of porogen diameter.

Some embodiments provide methods for forming a degradable, porous, photopatterned hydrogel. Suitable degradable crosslinking agents for forming degradable, porous, photopatterned hydrogels are as described above for the methods for forming degradable, photopatterned hydrogels. The porous, photopatterned hydrogels formed according to the methods of the invention may have a thickness greater than about 25 micrometers, such as a thickness between about 50 micrometers and about 1200 micrometers, or between about 100 micrometers and about 800 micrometers. The methods for forming porous or non-porous photopatterned hydrogels may further comprise the covalently or non-covalently immobilizing biologically active molecules in the hydrogel.

The porous or non-porous photopatterned hydrogels formed according to the methods of the invention are useful in a variety of medical applications, including, but not limited to, scaffolds for tissue engineering and repair, drug delivery, as angiogenic membranes, microfluidics, bioMEMs, coating, immobilization of biomolecules to surfaces with spatial fidelity, devices for microscale chromatography and electrophoresis, including biomolecules, applications in oligonucleotide arrays, proteomics, electrode arrays, and immobilization of cells and organisms.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A shows a top view of a photomask in which the printed pattern is shaded; FIG. 1B shows a side view of the photopatterning process in which a configuration of polymerization solution between two glass slides is irradiated through a photomask to form a patterned hydrogel from the solution under the dark regions of the photomask, while the solution under the transparent regions of the photomask is partially polymerized and remains soluble. FIG. 1C shows a top view of the patterned hydrogel formed using the photomask shown in FIG. 1A.

FIGS. 2B and C are scanning electron micrographs. The scale bars in FIGS. 2B and C represent 500 micrometers, and 200 micrometers, respectively.

DETAILED DESCRIPTION OF THE PREFERRED EMBODIMENT

Figure 1A:
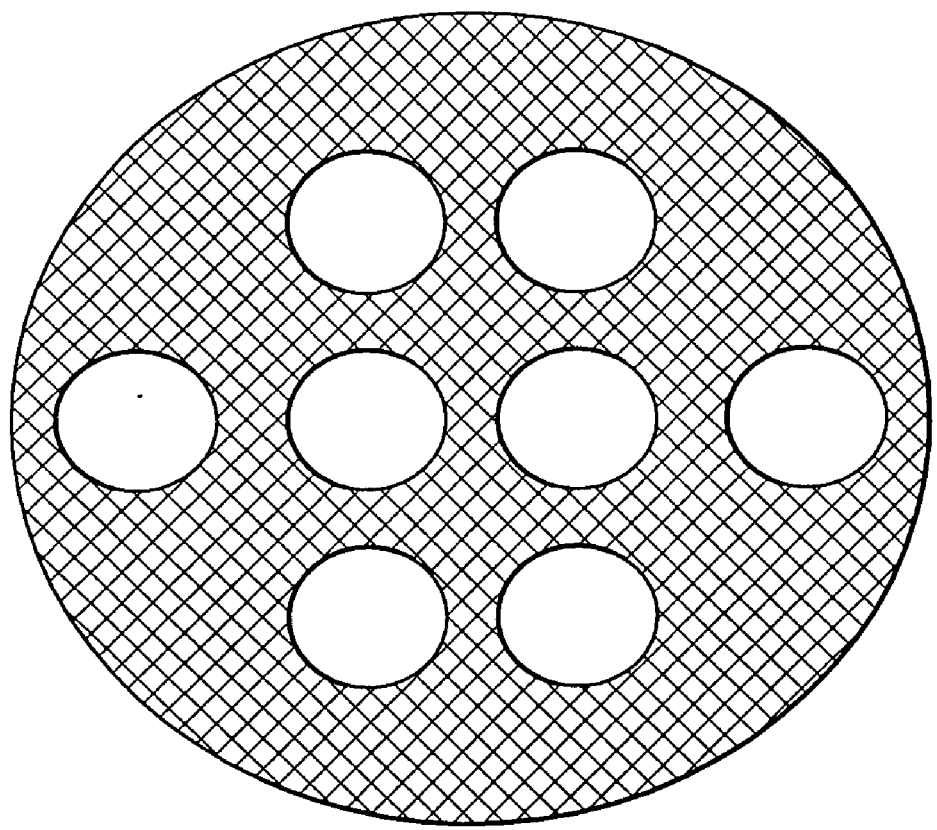
FIGS. 1A–C provides a schematic representation of the photopatterning process according to one embodiment of the methods of the invention, as described in EXAMPLE 1.

Unless specifically defined herein, all terms used herein have the same meaning as they would to one skilled in the art of the present invention.

One aspect of the invention provides methods for forming photopatterned hydrogels. Crosslinked hydrogels formed from free radical polymerizations undergo distinct features during polymerization. Free radical photopolymerization reactions undergo three primary reaction mechanisms: photoinitiation, propagation and termination. During photoinitiation, photoinitiator molecules absorb photons of light energy, dissociate into radicals that then react with monomer to form growing kinetic chains (or macroradicals). The rate of photoinitiation ($R_i$) is defined by $$R_i = 2\phi I_a$$

where $\phi$ is the overall photoinitiator efficiency; $I_a$ is the absorbed light intensity (moles of light quanta·L$^{-1}$·s$^{-1}$). In thick samples, $I_a$ will vary with sample thickness and can be defined by $$I_a = I_o(1 - e^{-2.303\epsilon c^* b})$$

where $\epsilon$ is the molar absorptivity of the initiator (L·mol$^{-1}$·cm$^{-1}$); and $c^*$ is the instantaneous photoinitiator concentration (mol·L$^{-1}$); and b is the sample thickness (cm). The choice of initiator, initiator concentration and light intensity are all factors that directly affect the rate of photoinitiation. Applying the pseudosteady state assumption where the rate of initiation is equal to the rate of termination, the rate of polymerization ($R_p$) is defined by $$R_p = k_p[M]\left(\frac{R_i}{2k_t}\right)^{1/2}$$

where $k_p$ is propagation kinetic constant, [M] is the double bond concentration, and $k_t$ is the termination kinetic constant. Termination typically occurs through biomolecular termination when two macroradicals terminate either through combination or disproportionation. The average length of the kinetic chain (v) is determined by the competition between propagation and termination and can be defined by $$v = \frac{R_p}{R_t}$$

As the kinetic chains grow during polymerization, the viscosity of the solution increases. This increase in viscosity leads to a reduction in the mobility of the growing kinetic chains or macroradicals. As a result, these macroradicals are unable to diffuse together and terminate. Subsequently, termination becomes diffusion controlled. The small monomer molecules can readily diffuse and propagation continues. As a result, the polymerization rate dramatically increases causing an autoacceleration effect. As the polymerization proceeds, diffusion of both macroradicals and monomers become diffusion controlled and the rate of polymerization drops rapidly causing an autodecceleration effect. These phenomena are characteristic of chain polymerizations of crosslinked systems. Thus, they do not only apply to radical chain polymerizations initiated by photoinitiators, but are also relevant to radical chain polymerizations using other initiators, such as thermal initiators or redox initiators.

The methods of the invention take advantage of the polymerization behavior to generate patterns in poly (HEMA) hydrogels. The basis for these methods is that polymerization is initiated across the monomer solution, but at different rates. When the difference is significant, some regions become crosslinked while at the same polymerization time, other regions are only partially polymerized, yet soluble. As a result, monomer molecules are being consumed across the sample. This phenomenon is contrary to conventional photopatterning of liquid phase solutions, where the dark regions are filled with a high concentration of monomer in which the propagating kinetic chains that diffuse into the dark regions can readily find a monomer and react resulting in propagation into the dark region. Using the methods of the invention, the probability that a propagating chain will encounter a monomer is significantly reduced due to the consumption of monomers across the system. As a result, the methods of the invention allow patterning at greater depths.

Accordingly, some embodiments of the methods of the invention comprise the step of exposing a solution comprising a monomer, a crosslinking agent, and a photoinitiator to a pattern of light comprising a first and a second light intensity for a period of time and under suitable conditions for the first light intensity to induce essentially complete conversion of polymerizable groups on the monomer and the crosslinking agent to form a patterned hydrogel, and for the second light intensity to induce partial conversion of polymerizable groups on the monomer and the crosslinking agent to form polymers that remain soluble. The first light intensity is generally lower than the second light intensity. In some embodiments, the monomer, crosslinking agent, and photoinitiator used in the methods of the invention are suitable for forming a hydrogel that is biocompatible and/or degradable. A schematic representation of an exemplary embodiment of the photopatterning is shown in FIG. 1.

The term "photopatterned hydrogel" or "patterned hydrogel" refers to a hydrogel that is photopolymerized using the methods of the invention and includes porous and non-porous hydrogels, as well as degradable and non-degradable hydrogels. The term "polymerization" refers to the reaction by which monomer molecules combine to form polymer molecules. The term "polymerizable group" refers to a group on the monomer or crosslinking agent that can link to another monomer or crosslinking agent to form a polymer. For example, the polymerizable group may be a methacrylate or an acrylate group, as described below. As used herein, "conversion" refers to the fraction of polymerizable groups on the monomer and the crosslinking agent that have been incorporated into a polymer (and subsequent hydrogel), which may be determined, for example, by monitoring the fraction of vinyl groups that have been incorporated into the polymer, as described in EXAMPLE 1. "Essentially complete conversion" refers to an extent of conversion that is sufficient to form a patterned hydrogel, whereas "partial conversion" refers to an extent of conversion that is insufficient to form a patterned hydrogel and instead results in polymer molecules that remain soluble. Typically, "essentially complete conversion" represents between about 90% and about 100% conversion, and "partial conversion" represents between about 1–40% conversion.

Any monomer with at least one polymerizable group may be used in the methods of the invention. Typically, the polymerizable group on the monomer is a methacrylate group or an acrylate group. Monomers that are suitable for use in the methods of the invention include, but are not limited to, methacrylates derivatives, such as 2-hydroxyethyl methacrylate, methyl methacrylate, methacrylic acid, n-butyl methacrylate, glycidyl methacrylate, n-propyl methacrylate, poly(ethylene glycol)monomethacrylate; acrylate derivatives, such as 2-hydroxyethyl acrylate, 2-methoxyethyl acrylate, acrylic acid, n-butyl acrylate, glycidyl acrylate, n-propyl acrylate, poly(ethylene glycol)monoacrylate; other monomers, such as ethylene, dienes, styrenes, halogenated olefins, vinyl esters, acrylonitriles, acrylamides, n-vinyl pyrrolidones; and mixtures thereof.

Any crosslinking agent that has at least two polymerizable groups may be used in the methods of the invention. Typically, the polymerizable groups on the crosslinking agent are methacrylate or acrylate groups. Suitable crosslinking agents include, but are not limited to, tetraethylene glycol dimethacrylate, tetraethylene glycol diacrylate, ethylene glycol dimethacrylate, ethylene glycol diacrylate, dipropylene glycol dimethacrylate, dipropylene glycol diacrylate, poly(ethylene glycol)dimethacrylate, poly(ethylene glycol)diacrylate, and mixtures thereof. Other suitable crosslinking agents are crosslinking agents that contain more than two polymerizable groups, such as bisacrylamide.

In some embodiments, the photopatterned hydrogels formed according to the methods of the invention are degradable. Degradable, photopatterned hydrogels are typically formed using degradable crosslinking agents, such as hydrolytically degradable crosslinking agents or enzymatically degradable crosslinking agents. Hydrolytically degradable crosslinking agents that may be used for forming degradable, photopatterned hydrogels include, but are not limited to, poly(ε-caprolactone)-b-tetraethylene glycol-b-poly(ε-caprolactone)dimethacrylate, poly(ε-caprolactone)-b-poly(ethylene glycol)-b-poly(ε-caprolactone)dimethacrylate, poly(lactic acid)-b-tetraethylene glycol-b-poly(lactic acid)dimethacrylate, poly(lactic acid)-b-poly(ethylene glycol)-b-poly(lactic acid)dimethacrylate, poly(glycolic acid)-b-tetraethylene glycol-b-poly(glycolic acid)dimethacrylate, poly(glycolic acid)-b-poly(ethylene glycol)-b-poly(glycolic acid)dimethacrylate, poly(ε-caprolactone)-b-tetraethylene glycol-b-poly(ε-caprolactone)diacrylate, poly(ε-caprolactone)-b-poly(ethylene glycol)-b-poly(ε-caprolactone)diacrylate, poly(lactic acid)-b-tetraethylene glycol-b-poly(lactic acid) diacrylate, poly(lactic acid)-b-poly(ethylene glycol)-b-poly(lactic acid) diacrylate, poly(glycolic acid)-b-tetraethylene glycol-b-poly(glycolic acid)diacrylate, poly(glycolic acid)-b-poly(ethylene glycol)-b-poly(glycolic acid) diacrylate, and mixtures thereof. Enzymatically degradable crosslinking agents that may be used for forming degradable, photopatterned hydrogels include, but are not limited to, crosslinking agents in which a short sequence of amino acids (for example, 3–5 amino acids) are linked to two methacrylate or acrylate groups. Examples of enzymatically degradable crosslinking agents include, but are not limited to, alanine-proline-glycine-leucine-poly(ethylene glycol)-alanine-proline-glycine-leucine)-diacrylate, alanine-proline-glycine-leucine-diacrylate, alanine-proline-glycine-leucine-poly(ethylene glycol)-alanine-proline-glycine-leucine)-dimethylacrylate, and alanine-proline-glycine-leucine-dimethylacrylate (West & Hubbell (1999) *Macromolecules* 32(1):241–4). An exemplary methods for forming degradable, photopatterned hydrogel is described in EXAMPLES 2 and 4.

Any photoinitiator that is photoactivatable may be used in the methods of the invention. Suitable photoinitiators include, but are not limited to, 2,2-dimethoxy acetophenone, 1-hydroxycyclohexyl phenyl ketone, 2-methyl-1-[4-(methylthio)phenyl]-2-(4-morpholinyl)-1-propoanone, 2-hydroxy-1-[4-(hydroxyethoxy)phenyl]-2-methyl-1-propanone, and mixtures thereof.

The solution comprising a monomer, a crosslinking agent, and a photoinitiator (i.e., the polymerization solution) is exposed to a pattern of light, typically through a photomask. The pattern of light is a spatial pattern and comprises a first and a second light intensity. Generally, the first light intensity is lower than the second light intensity. As described above, an increase in light intensity results in an increase in the number of initiating radicals resulting in an increase in the number of propagating chains, but shorter chains. As a result, vitrification effects are delayed which in turn delay autoacceleration and cause longer polymerization times.

The solution comprising a monomer, a crosslinking agent, and a photoinitiator is exposed to the light pattern for a period of time and under suitable conditions for the first light intensity to induce essentially complete conversion of polymerizable groups on the monomer and the crosslinking agent to form a patterned hydrogel, and for the second light intensity to induce partial conversion of polymerizable groups on the monomer and the crosslinking agent to form polymers that remain soluble. For any given polymerization solution, there exists an optimal light intensity that results in the shortest exposure times required to convert the liquid solution to a crosslinked hydrogel, whereas light intensities that are higher or lower require longer exposure times. As a result, a patterned material can be generated from the polymerization solution by effectively modulating the light intensity, for example, through the opacity of a photomask. In essence, for a given exposure time, the regions that receive the optimal light intensity reach complete conversion (and thus form a highly crosslinked hydrogel) while regions receiving less than optimal light intensity (e.g., high light intensities) result in a partially polymerized, yet not completely crosslinked, solution that can be washed away. Thus, the chain polymerization reaction is occurring throughout the sample, but there is a sufficient difference in the polymerization kinetics induced by the different light intensities to develop a patterned hydrogel.

Accordingly, the methods of the invention may be used for forming patterned hydrogels from any solution comprising a monomer, a crosslinking agent, and a photoinitiator, provided there is a sufficient difference in the polymerization kinetics for a defined exposure time and initiator concentration to induce essentially complete conversion at a first light intensity and partial conversion at a light second intensity. Suitable conditions for forming a patterned hydrogel according to the methods of the invention and suitable times of exposure to a light pattern may be readily determined for any solution containing a monomer, a crosslinking agent, and a initiator, as well as different concentrations thereof, by monitoring the polymerization and crosslinking kinetics after exposing the polymerization solution to different light intensities for different periods of time. Methods for monitoring polymerization and crosslinking kinetics are standard in the art. Exemplary methods for monitoring polymerization and crosslinking kinetics are described in EXAMPLE 1. For example, exposing a solution comprising 83% (v/v) 2-hydroxyethyl methacrylate, 2 mol % tetraethylene glycol dimethacrylate, and 1% (w/w) 2,2-dimethoxy acetophenone through a photomask of 93% opacity—corresponding to an incident light intensity of 45 mW/cm$^2$—resulted in 96±3% conversion in 30 seconds, whereas a photomask of 0% opacity (i.e. clear)—corresponding to 850 mW/cm$^2$—resulted in 29±0.004% conversion at 30 seconds and 95±5% conversion in 300 seconds, as described in EXAMPLE 1. The term "incident light intensity" refers to the light intensity at the top surface of the solution. A representative method for measuring incident light intensities is provided in EXAMPLE 1. In some embodiments, suitable incident light intensities for use in the methods of the invention are between about 1 mW/cm$^2$ and about 1000 mW/cm$^2$. In some embodiments, suitable periods of time for exposing the solution are between about 2 seconds and about 120 seconds.

In some embodiments, the methods comprise the step of exposing a solution comprising a monomer, a crosslinking agent, and a photoinitiator to a pattern of light comprising a first and a second light intensity for a period of time under suitable conditions to form a photopatterned hydrogel defined by regions of the solution exposed to the first light intensity, wherein the first light intensity is lower than the second light intensity. Suitable monomers, crosslinking agents, photoinitiators, and conditions for forming a photopatterned hydrogel are as described above.

Using the methods of the invention, patterned pHEMA hydrogels and patterned porous pHEMA hydrogels have been fabricated with a range of monomer formulations. For example, solutions with different concentrations of monomer (for example, ranging from 57% (v/v) HEMA up to 83% (v/v) HEMA) resulted in patterned hydrogels. The size and structure of the patterned hydrogels may be varied simply through the design of the pattern of light intensities to achieve a desired hydrogel pattern.

The methods of the invention allow the formation of thicker photopatterned hydrogels than is possible using prior photopatterning methods. In some embodiments, the photopatterned hydrogels formed according to the methods of the invention have a thickness greater than about 25 micrometers, such as a thickness of between about 50 micrometers and about 1200 micrometers, or between about 100 micrometers and about 800 micrometers. For example, photopatterned poly(HEMA)hydrogels with a thickness of 760 micrometers, as described in EXAMPLE 1, or a thickness of 1100 micrometers, as described in EXAMPLE 2.

Another aspect of the invention provides methods for forming a porous, photopatterned hydrogel. In some embodiments, the methods comprise the steps of: (a) exposing a plurality of porogens in a solution comprising a monomer, a crosslinking agent, and a photoinitiator to a pattern of light comprising a first and a second light intensity for a period of time and under suitable conditions for the first light intensity to induce essentially complete conversion of polymerizable groups on the monomer and the crosslinking agent to form a patterned hydrogel, and for the second light intensity to induce partial conversion of polymerizable groups on the monomer and the crosslinking agent to form partially polymerized polymers that remain soluble; and (b) removing the plurality of porogens to form a porous, photopatterned hydrogel.

Suitable monomers, cross-linking agents, photoinitiators, and conditions for forming a photopatterned hydrogel are as described above for the first aspect of the invention.

As used herein, the term "porogens" refers to any structures that can be used to create a template that is removable after the photopatterned hydrogel is formed under conditions that do not destroy the hydrogel. Exemplary porogens that are suitable for use in the methods of the invention include, but are not limited to, polymer particles such as PMMA beads and polystyrene beads. The porogens may have a range of sizes. For example, the porogens may have a mean diameter between about 20 and about 200 micrometers.

In some embodiments, the plurality of porogens may be formed into a template using any suitable method known in the art. For example, a template may be formed by packing the porogens into a mold. A suitable mold may be formed, for example, by using two glass microscope slides separated by spacers. The porogens may be packed into a mold using ultrasonic agitation or any other suitable method for obtaining a closely packed array of porogens. The porogens may then be fused to form connections between the porogens, for example, by sintering. Suitable porogens and methods for forming a template are described in PCT/US2004/032639, filed Oct. 1, 2004, herein incorporated by reference.

After a photopatterned hydrogel has been formed around the porogens, the porogens are removed to produce the porous, patterned hydrogel. In some embodiments, the porogens are removed by solvent extraction, for example, an extraction with an acetone-water solution. Exemplary methods for forming a photopatterned, porous hydrogel are described in EXAMPLES 3 and 4.

In some embodiments of the methods of the invention, porous, photopatterned hydrogels may be formed by using a salt (for example, NaCl), a sugar, or wax of the desired size as porogens, forming a hydrogel around them as described above, and then removing porogen, for example by solvent extraction.

Accordingly, the methods of the invention may be used to form a photopatterned, porous hydrogel with a range of pore sizes and a variety of 3D macro-architectures. The pore sizes of the porous patterned hydrogels may be varied simply through the choice of porogen diameter.

In some embodiments, the methods comprise the steps of: (a) exposing a plurality of porogens in a solution comprising a monomer, a crosslinking agent, and a photoinitiator to a pattern of light comprising a first and a second light intensity for a period of time under suitable conditions to form a photopatterned hydrogel defined by regions of the solution exposed to the first light intensity, wherein the first light intensity is lower than the second light intensity; and (b) removing the plurality of porogens to form a porous, photopatterned hydrogel.

The patterned hydrogels formed according to the methods of the invention can be used in a variety of medical applications where an inexpensive and rapid patterning technique is required for non-porous and porous materials. Such applications include, but are not limited to, scaffolds for tissue engineering and repair, drug delivery, angiogenic membranes, microfluidics, bioMEMs, coating, immobilization of biomolecules to surfaces with spatial fidelity, devices for microscale chromatography and electrophoresis, including biomolecules, applications in oligonucleotide arrays, proteomics, electrode arrays, and immobilization of cells and organisms. The macroscopic properties of these materials can readily be controlled to function in a variety of different applications. For example, simple variations in the monomer solution, such as an increase crosslinker concentration, will result in increased gel modulus or slower drug delivery. Channels of varying size can be patterned into the hydrogel for use as microfluidic devices. Porous hydrogels can be patterned and used in chip arrays.

As described above, hydrolysable or enzymatically susceptible linkages may also be incorporated into the hydrogel for controlled degradation. In addition, the methods of the invention may be readily adapted to immobilize covalently or non-covalently a variety of biologically active molecules, such as proteins, drugs, and other therapeutic agents, for example, to enhance cell interaction. In some embodiments, hydroxyapatite may be added to the hydrogel for use in bone repair and bone tissue engineering. Biologically active molecules may be introduced into the patterned hydrogels by forming the hydrogels in the presence of the biologically active molecules, by allowing the biologically active molecules to diffuse into the patterned hydrogels, or by otherwise introducing the biologically active molecules into the patterned hydrogels. For example, natural polymers and other biologically active molecules, including, but not limited to, collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, etc., may be added to the polymerization solution prior to polymerization. Upon polymerization, these biologically active molecules are entrapped in the hydrogel, providing biocompatibility and/or biological functions to the hydrogel. Using the methods of the invention, an ECM adhesive protein, collagen type I, was incorporated into porous, degradable, photopatterned pHEMA hydrogels by simply adding the protein to the polymerization formulation to create a cell adhesive hydrogel, as described in EXAMPLE 4. The incorporation of collagen type I promoted adhesion and spreading of skeletal myoblasts throughout the pores of a porous, degradable, photopatterned hydrogel, as described in EXAMPLE 4.

Many useful functional groups can be inserted into the system by virtue of the pendant hydroxyl groups on the polymer (poly(2-hydroxyethyl methacrylate)). This offers a method to covalently immobilize proteins, drugs, and other therapeutic agents. For example, these proteins, drugs, and other therapeutic agents may interact with cells seeded onto the hydrogel. The hydroxy functional groups can be chemically coupled by a variety of common chemistries, including but not limited to, carbonyl diimidazole derivatization.

Any reactive functional group present on polymer molecules within the patterned hydrogel formed using the methods of the invention can be used to covalently attach biologically active molecules to the hydrogels. The following publications, incorporated herein by reference, describe examples of technologies that are useful for attaching biologically active molecules to polymer molecules: Nuttelman et al. (2001) *J. Biomed. Mater. Res.* 57:217–223; Rowley et al. (1999) *Biomaterials* 20:45–53; Hubbell (1995) *Biotechnology* 13:565–76; Massia & Hubbell (1990) *Anal. Biochem*

187:292–301; Drumheller et al. (1994) *Anal. Biochem.* 222:380–8; Kobayashi & Ikada (1991) *Curr. Eye Res.* 10:899–908; Lin et al. (1992) *J. Biomaterial Sci. Polym. Ed.* 3:217–227; and Bellamkonda et al. (1995) *J. Biomed. Mater. Res.* 29:663–71.

Biocompatible patterned hydrogels formed using the methods of the invention may be applied to, or formed on, any implantable medical device, including, but not limited to, chemical sensors or biosensors (such as devices for the detection of analyte concentrations in a biological sample), cell transplantation devices, drug delivery devices such as controlled drug-release systems, electrical signal delivering or measuring devices, prosthetic devices, and artificial organs. The hydrogel improves the biocompatibility of the implanted medical device (such as the biocompatibility and communication of neuroelectrodes and pacemaker leads with surrounding tissues), improves the sealing of skin to percutaneous devices (such as in-dwelling catheters or transcutaneous glucose sensors), enhances tissue integration, and provides barriers for immunoisolation of cells in artificial organs systems (such as pancreatic cells devices), and improves the healing of vessels after balloon angioplasty and stent placement.

In some embodiments, the hydrogels may be formed directly on a medical device by applying the polymerization solution to the medical device and exposing it to a pattern of light intensities. Moreover, the patterned hydrogels formed using the methods of the invention may be immobilized onto (or within) a surface of an implantable or attachable medical device body. For example, the patterned hydrogels may be disposed over substantially the entire outer surface of the device body. The modified surface will typically be in contact with living tissue after implantation into an animal body. As used herein, "implantable or attachable medical device" refers to any device that is implanted into, or attached to, tissue of an animal body during the normal operation of the device (e.g., implantable drug delivery devices). Such implantable or attachable medical device bodies can be made from, for example, nitrocellulose, diazocellulose, glass, polystyrene, polyvinylchloride, polypropylene, polyethylene, dextran, Sepharose, agar, starch, and nylon. Linkage of the hydrogel to a device body can be accomplished by any technique that does not destroy the desired properties of the hydrogel. For example, a surface of an implantable or attachable medical device body can be modified to include functional groups (e.g., carboxyl, amide, amino, ether, hydroxyl, cyano, nitrido, sulfanamido, acetylinic, epoxide, silanic, anhydric, succinimic, azido) for immobilizing a hydrogel thereto. Coupling chemistries include, but are not limited to, the formation of esters, ethers, amides, azido and sulfanamido derivatives, cyanate and other linkages to functional groups available on the hydrogel.

A surface of a device body that does not possess useful reactive groups can be treated with radio-frequency discharge plasma (RFGD) etching to generate reactive groups (e.g., treatment with oxygen plasma to introduce oxygen-containing groups; treatment with propyl amino plasma to introduce amine groups). When RFGD glow discharge plasma is created using an organic vapor, deposition of a polymeric overlayer occurs on the exposed surface. RFGD plasma deposited films offer several unique advantages. They are smooth, conformal, and uniform. Film thickness is easily controlled and ultrathin films (10–1000 Angstroms) are readily achieved, allowing for surface modification of a material without alteration to its bulk properties. Moreover, plasma films are highly-crosslinked and pin-hole free and therefore chemically stable and mechanically durable. RFGD plasma deposition of organic thin films has been used in microelectronic fabrication, adhesion promotion, corrosion protection, permeation control, as well as biomaterials (see, e.g., U.S. Pat. No. 6,131,580).

Some medical devices are adapted to be implanted into the soft tissue of an animal, such as a mammal, including a human, during the normal operation of the medical device. Implantable medical devices comprising patterned hydrogels formed using the methods of the invention may be completely implanted into the soft tissue of an animal body (i.e., the entire device is implanted within the body), or the device may be partially implanted into an animal body (i.e., only part of the device is implanted within an animal body, the remainder of the device being located outside of the animal body). Representative examples of completely implantable medical devices include, but are not limited to: cardiovascular devices (such as vascular grafts and stents), artificial blood vessels, artificial bone joints, such as hip joints, and scaffolds that support tissue growth (in such anatomical structures as nerves, pancreas, eye and muscle). Representative examples of partially implantable medical devices include: biosensors (such as those used to monitor the level of drugs within a living body, or the level of blood glucose in a diabetic patient) and percutaneous devices (such as catheters) that penetrate the skin and link a living body to a medical device, such as a kidney dialysis machine.

Some medical devices of the invention are adapted to be affixed to soft tissue of an animal, such as a mammal, including a human, during the normal operation of the medical device. These medical devices are typically affixed to the skin of an animal body. Examples of medical devices that are adapted to be affixed to soft tissue of an animal include skin substitutes and wound or burn treatment devices (such as surgical bandages and transdermal patches). The presence of a biocompatible, patterned hydrogel on the device body of a medical device will reduce or eliminate the foreign body response to the device body after implantation into, or attachment to, tissue of an animal body.

The medical devices may further comprise biologically active molecules within the patterned hydrogel attached to the device body to provide for the controlled delivery of drugs and other biologically active molecules, such as DNA, RNA, or proteins. The biologically active molecules may be attached, covalently or non-covalently, to the crosslinking molecules or polymer molecules in the hydrogel, as described above.

The biologically active molecules can be attached to every part of the device, or to only a portion of the device. For example, in some embodiments that are adapted to be implanted into an animal, biologically active molecules that act to decrease the foreign body reaction (e.g., anti-inflammatory agents, and immunomodulatory agents) are attached only to the surface(s) of the device that is/are in contact with living tissue in the animal body. The biologically active molecules serve to decrease the foreign body reaction of the living body against the implanted structure.

The following examples merely illustrate the best mode now contemplated for practicing the invention, but should not be construed to limit the invention.

EXAMPLE 1

This example describes an exemplary method of the invention for forming photopatterned hydrogels.

A. Materials and Methods

Photomask: Photomasks with different opacities were created using transparency film in order to determine the difference in polymerization kinetics required to achieve a pattern. Photomasks were designed using Freehand Version 8 and printed onto a transparency film using a high-resolution printer with 3600 dpi. Initially, solid colored transparency films were produced with a range of opacities, where 0% opacity is clear and 100% opacity is black. The transmittance of 365 nm light was monitored for each mask opacity using a U/VIS spectrophotometer.

Photopolymerization: 2-Hydroxyethyl methacrylate (HEMA, Polysciences, Inc.), tetraethylene glycoldimethacrylate (TEGDM, Polysciences, Inc.) and 2,2-dimethoxy-2-phenylacetophenone (DMPA, Ciba-Geigy) were used as received. A monomer solution was prepared with 57–83% (v/v) 2-hydroxyethyl methacrylate (HEMA, Polysciences, Inc.); a crosslinker molecule, 2 mol % tetraethylene glycol dimethacrylate (Polysciences, Inc.) per mol HEMA; a photoinitiator, 1.5% (w/w) 2,2-dimethoxy acetophenone (Ciba Geigy) in a solution of ethylene glycol (Fisher Scientific, Inc.) and distilled water (1:1.3 ratio). The monomer solution was purged with nitrogen for several minutes. The polymerization configuration contained monomer solution placed in a Teflon mold (7 mm diameter punched hole, 760 micrometers thick) that was sandwiched between two glass slides held together with binder clips. Prior to placing the monomer solution in the Teflon mold, the glass slides were pretreated with glycerol to facilitate removal of the gel from the configuration after polymerization.

The photomask was placed on top of the glass slide as shown in FIG. 1. This configuration was placed 1 cm below the light guide equipped with a collimating lens adaptor that was connected to a UV light source (Novacure Model 2100, Exfo, Inc.) containing a 365 nm bandpass filter. The light intensity was set at 4300 mW/cm$^2$. Light is transmitted across the mask, but at different intensities depending on the mask opacity. The dark regions absorb a significant amount of the light intensity, whereas the clear regions transmit a higher light intensity. A radiometer was used to measure the light attenuation from 1 cm below the light guide. Light transmittance through the transparency film and glass slide was measured using a U/VIS spectrophotometer at 365 nm. Light attenuation due to the 1 cm distance, the transparency film and glass slide resulted in an incident light intensity of 850 mW/cm$^2$. The incident light intensity was determined for each polymerizing sample.

Immediately after polymerization, the configuration was dipped in an acetone/dry ice bath for 2 seconds, then placed in a methanol/ice bath for several minutes while removing the crosslinked gel from the configuration.

To investigate the effects of an inhibitor, copper chloride was added to the monomer solution at a concentration of 0.26% (w/w). This solution was polymerized under the 93% opacity mask and conversion was measured using NIR.

Near Infrared Spectroscopy: Near infrared (NIR) spectroscopy (Bruker Vector) was used to quantify conversion by monitoring the disappearance of the vinyl group on the monomer and crosslinker after exposing to light. Conversion was calculated by subtracting the ratio of the vinyl peak area (6100–6300 cm$^{-1}$) of the polymerized sample to the vinyl peak area of the initial non-polymerized sample from one (n=3). The conversion of double bonds was calculated by subtracting the ratio of the peak area of the polymerized sample to the peak area of the initial, non-polymerized sample from one.

Gel permeation chromatography: Gel permeation chromatography (GPCmax VE2001, Viscotec) equipped with a RI detector 3580 was used to determine the molecular weights of the growing kinetic chains during polymerization. Samples were run in dimethylformamide with 1 wt % LiBr at a flow rate of 1 ml/min at 35° C. and compared against linear poly(methylmethacrylate) standards. The columns used were Tosoh Bioscience alpha-3000 and alpha-4000.

Differential Scanning Calorimetry: The rate of polymerization was monitored using differential scanning calorimetry (DSC, Perkin Elmer DSC-7). The DSC head was removed and a glass slide placed over the sample pans to enable transmission of the initiating light to the sample pan. The modified configuration did not affect the instrument's ability to maintain a constant temperature. The light guide was placed over the sample pan. Light intensity was measured by placing carbon discs (5 mm in diameter) flow. In the absence of monomer solution, heat flow was measured from the light source. Approximately 3 mg of monomer solution was placed in the sample pan. Quartz discs were placed over the monomer solution to prevent evaporation. The sample was allowed to equilibrate for several minutes prior to turning on the light source. The heat flow associated with the light was subtracted from the heat flow associated with the polymerization reaction.

Scanning Electron Microscopy: Samples were dried under vacuum overnight. The dried samples were visualized using scanning electron microscopy (FEI Sirion 30) with a beam voltage of 1 kV.

B. Results

When a solution containing 83% (v/v) 2-hydroxyethyl methacrylate, 2 mol % tetraethylene glycol dimethacrylate, and 1% (w/w) 2,2-dimethoxy acetophenone was exposed to 365 nm light for 30 seconds through a photomask in which the desired pattern was presented in 93% opacity and the remaining mask was 0% opacity, a patterned hydrogel resulted in which the patterned features of solid hydrogel were formed only behind the 93% opacity regions of the photomask, i.e., regions of low light intensity. FIG. 1 depicts schematically the photopatterning process.

This finding was verified by monitoring the polymerization reaction through the disappearance of the vinyl group on the monomer using near infrared (NIR) spectroscopy. The monomer solution was exposed to longwave UV light for 30 seconds using photomasks with different opacities to determine the influence of light intensity on the polymerization reaction, specifically double bond conversion. The results are shown in Table 1. When the mask opacities were between 85 and 93%, about 100% conversion was reached. However, masks with higher and lower opacities resulted in conversions less than 100%.

TABLE 1

Conversion of Methacrylate at 30 Seconds as a Function of Photomask Opacity.

| Conversion at 30 Seconds | % Opacity of Photomask |
|---|---|
| 0.29 ± 0.004 | 0 |
| 0.41 ± 0.002 | 50 |
| 0.68 ± 0.07 | 75 |
| 0.74 ± 0.11 | 80 |
| 0.99 ± 0.005 | 85 |
| 0.98 ± 0.01 | 90 |
| 0.96 ± 0.03 | 93 |
| 0.70 ± 0.14 | 95 |
| 0.35 ± 0.04 | 98 |
| 0.18 ± 0.02 | 100 |

The transmittance of 365 nm light was monitored for each mask opacity using a UV/VIS spectrophotometer and the incident light intensity was determined for each polymerizing sample. The opacity of the photomasks was directly proportional to the light intensity as shown in Table 2. Light intensity in Table 2 is the incident light intensity ($I_o$) calculated from the transmitted light intensity of the photomask and the configuration of the polymerization set-up. For example, a mask of 0% opacity resulted in an $I_o$ of 850 mW/cm² while 93% opacity mask resulted in an $I_o$ of 45 mW/cm².

TABLE 2

Incident Light Intensity at 365 nm at Sample Surface as a Function of Percent Opacity of Photomask.

| Light Intensity at 365 nm (mW/cm²) | % Opacity of Photomask |
|---|---|
| 850 | 0 |
| 450 | 50 |
| 215 | 75 |
| 165 | 80 |
| 120 | 85 |
| 80 | 90 |
| 45 | 93 |
| 30 | 95 |
| 0.0 | 98 |
| 0.0 | 100 |

In general, the rate of polymerization will increase with increases in light intensity resulting in faster conversions for a given exposure time (Goodner et al. (1999) *Macromolecules* 32:6552–9). An increase in double bond conversion was observed with a decrease in mask opacity from 100 to 93%, corresponding to an increase in light intensity. It should be noted that since these masks are prepared on transparency film, a small amount of light will transmit through the 100% opacity mask initiating polymerization. However, mask opacities less than 85%, corresponding to $I_o$ greater than 120 mW/cm², resulted in decreased conversions with decreasing mask opacity. Interestingly, an optimal range of mask opacities between 85 and 93% resulted in near complete conversion (greater than 96%). The incident light intensity range that corresponds to the maxima in conversion is between 45 and 120 mW/cm². Conversion with the 0% opacity mask reached only 30% with a corresponding light intensity of 850 mW/cm².

To confirm that the difference in the conversion at 30 seconds was due to changes in the polymerization kinetics, two masks, 93% and 0% opacity, were chosen that represented high and low conversion, respectively, after a 30-second exposure. The polymerization reaction was monitored through its entirety and the results are given in Table 3.

Double bond conversion as a function of polymerization time was similar under both masks at early conversions, up to 20%. At longer polymerization times, conversion deviated. Under the 93% opacity mask, complete conversion was reached in 30 seconds while under the 0% opacity mask the polymerization reaction occurred at a slower rate resulting in complete conversion after 300 seconds. Therefore, the polymerization times for the two samples differed by 270 seconds. These data confirm that photomasks can be used to modulate the polymerization reaction through changes in light intensity.

TABLE 3

Conversion of Methacrylate as a Function of Exposure Time Using Different Photomask Opacities.

| Exposure Time (seconds) | Conversion Using 93% Opacity Photomask | Conversion Using 0% Opacity Photomask |
|---|---|---|
| 0 | 0 ± 0 | 0 ± 0 |
| 5 | 11.0 ± 1.3 | |
| 10 | 22.2 ± 1.7 | 21.8 ± 1.9 |
| 15 | 36.7 ± 2.8 | |
| 20 | 59.6 ± 11.7 | 27.5 ± 3.8 |
| 25 | 71.4 ± 21.5 | |
| 30 | 96.4 ± 3.3 | 29.2 ± 0.4 |
| 60 | | 36.5 ± 4.2 |
| 120 | | 60.5 ± 10.1 |
| 300 | | 95.1 ± 4.5 |

These results suggest that other factors begin to dominate the polymerization reaction with increases in light intensity. Upon irradiation, initiator molecules absorb photons of light energy and dissociate into radicals. A higher $I_o$ results in a greater number of radicals formed per unit time. Each radical formed will initiate a growing chain. As a result, a higher $I_o$ will initiate more chains after a given exposure time compared to a lower $I_o$ with a greater number of chains present, this observation can lead to shorter kinetic chains. Gel permeation chromatography was used to measure the molecular weight of the kinetic chains after a 10-second exposure for polymerization systems under the 0 and 93% opacity masks. At this exposure time, conversion was identical for systems polymerized under both masks. The results are given in Table 4. The kinetic chain length ($M_n$) was 2700±290 Da under the 0% opacity mask compared to 9200±100 Da under the 93% opacity mask. Although the molecular weight ($M_w$) was 3.4-fold lower, conversion was similar at 22% under both masks. The polydispersity index (PDI) was also significantly higher under the 0% opacity mask. The higher the PDI, the broader the molecular weight range is for the kinetic chains. To ensure that the high light intensity did not degrade the poly(HEMA), linear poly(HEMA) was exposed to UV light under the 0 and 93% opacity masks. The molecular weight of the poly(HEMA) was 170,000 Da after exposure to UV light under both mask opacities suggesting that the high $I_o$ associated with the 0% opacity mask did not adversely affect the growing chains.

TABLE 4

Kinetic Chain Length After 10 Seconds Exposure at 365 nm.

| Photomask Opacity (%) | $M_n$ | $M_w$ | Polydispersity Index |
|---|---|---|---|
| 0 | 2700 ± 290 | 25700 ± 7000 | 9.7 ± 2.9 |
| 93 | 9200 ± 100 | 32800 ± 1000 | 3.6 ± 0.2 |

Differential scanning calorimetry was used to measure the rate of polymerization under high and low light intensities associated with the 0 and 93% opacity masks. The results are shown in Table 5. A light intensity at 40 mW/cm² resulted in polymerization behavior characteristic of crosslinked systems exhibiting distinct autoacceleration and autodeceleration features. When a light intensity of 720 mW/cm² was used, the polymerization behavior had strikingly different features. The first noted feature is the lack of autoacceleration and autodeceleration.

TABLE 5

Normalized Heat Flow as a Function of Different Light Intensities.

| Normalized Heat Flow (W/g) | Light Intensity of 40 mW/cm$^2$ | Light Intensity of 720 mW/cm$^2$ |
|---|---|---|
| 0 | 2.66 | 1.41 |
| 5 | 14.5 | 9.6 |
| 10 | 16.1 | 10.3 |
| 15 | 21.6 | 10.5 |
| 20 | 18.0 | 10.6 |
| 25 | 6.91 | 10.7 |
| 30 | 4.01 | 10.8 |
| 40 | | 11.0 |
| 60 | | 11.5 |
| 80 | | 11.5 |
| 100 | | 11.5 |
| 160 | | 11.1 |
| 200 | | 10.9 |
| 240 | | 10.8 |
| 300 | | 10.7 |

The effect of adding an inhibitor (CuCl$_2$) on conversion under the 93% opacity mask is shown in Table 6. Copper chloride reacts with initiating radicals to inhibit the polymerization reaction.

TABLE 6

Effect of Inhibitor on Conversion as a Function of Exposure Time.

| Time (s) | Conversion Using 93% Opacity Photomask | Conversion Using 93% Opacity Photomask with Inhibitor | Conversion Using 0% Opacity Photomask |
|---|---|---|---|
| 0 | 0 ± 0 | 0 ± 0 | 0 ± 0 |
| 5 | 11.0 ± 1.3 | 2.2 ± 0.6 | |
| 10 | 22.2 ± 1.7 | 6.8 ± 1.2 | 21.8 ± 1.9 |
| 15 | 36.7 ± 2.8 | | |
| 20 | 59.6 ± 11.7 | 19.8 ± 0.5 | 27.5 ± 3.8 |
| 25 | 71.4 ± 21.5 | | |
| 30 | 96.4 ± 3.3 | 37.6 ± 3.0 | 29.2 ± 0.4 |
| 40 | | 70.4 ± 12.8 | |
| 60 | | 98.4 ± 0.4 | 36.5 ± 4.2 |

When a photomask similar to the one depicted in FIG. 1 (93% opacity with 0% opacity circles of 500 micrometer diameter spaced 2 mm apart) was used, and the liquid phase polymerization formulation was exposed to the initiating light for 30 seconds, a patterned hydrogel formed with a thickness of 760 micrometers. Scanning electron microscopy was used to visualize the patterned hydrogel. The pattern was preserved throughout the total thickness of the hydrogel.

EXAMPLE 2

This example describes an exemplary method of the invention for forming degradable, photopatterned hydrogels.

A. Materials and Methods

Photomasks: Photomasks were generated as described in EXAMPLE 1. The pattern shown in FIG. 1A was drawn with 93% opacity and the regions where open channels were desired were clear (i.e., 0% opacity).

Degradable Crosslinker: Hydrolytically labile crosslinker, poly(ε-caprolactone)-b-tetraethylene glycol-b-poly(ε-caprolactone)dimethacrylate was synthesized according to previously described techniques (Sawhney et al. (1993) *Macromolecules* 26(4): 581–587). Briefly, tetraethylene glycol (5 ml) was reacted with ε-caprolactone (15–25 ml) at 140° C. in the presence of stannous octoate for 6 hours under vacuum. The reaction was cooled to room temperature and diluted with methylene chloride (50 ml). Triethylamine was added to the reaction mixture in 1.25 molar excess. Methacryloyl chloride (1.25 molar excess) was added dropwise to the reaction mixture. The reaction was continued at 4° C. under nitrogen overnight and at room temperature for 24 hours. The final product, poly(ε-caprolactone)-b-tetraethylene glycol-b-poly(ε-caprolactone)dimethacrylate, was verified with $^1$H-NMR.

Polymerization: A monomer solution was prepared with 80% (v/v) 2-hydroxyethyl methacrylate (HEMA, Polysciences, Inc.); the degradable crosslinker molecule, 2–3 mol % poly(ε-caprolactone)-b-tetraethylene glycol-b-poly (ε-caprolactone)dimethacrylate per mol HEMA; a photoinitiator, 1.5% (w/w) 2,2-dimethoxy acetophenone (Ciba Geigy) in a solution of ethylene glycol and distilled water (1:1.3 ratio). The polymerization configuration is described in EXAMPLE 1.

Scanning Electron Microscopy: Scanning electron microscopy was performed as described in EXAMPLE 1.

B. Results

Figure 1B:
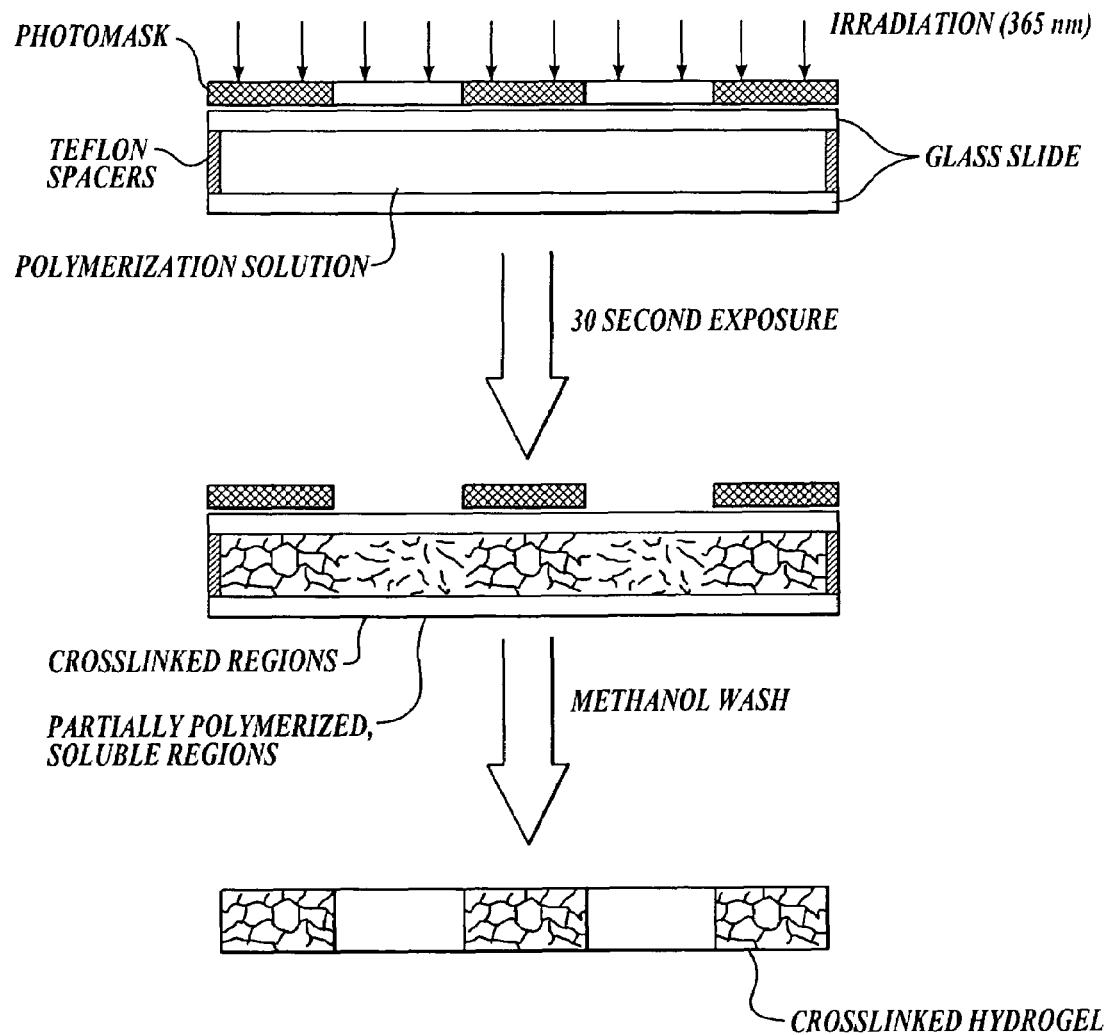
Figure 1C:
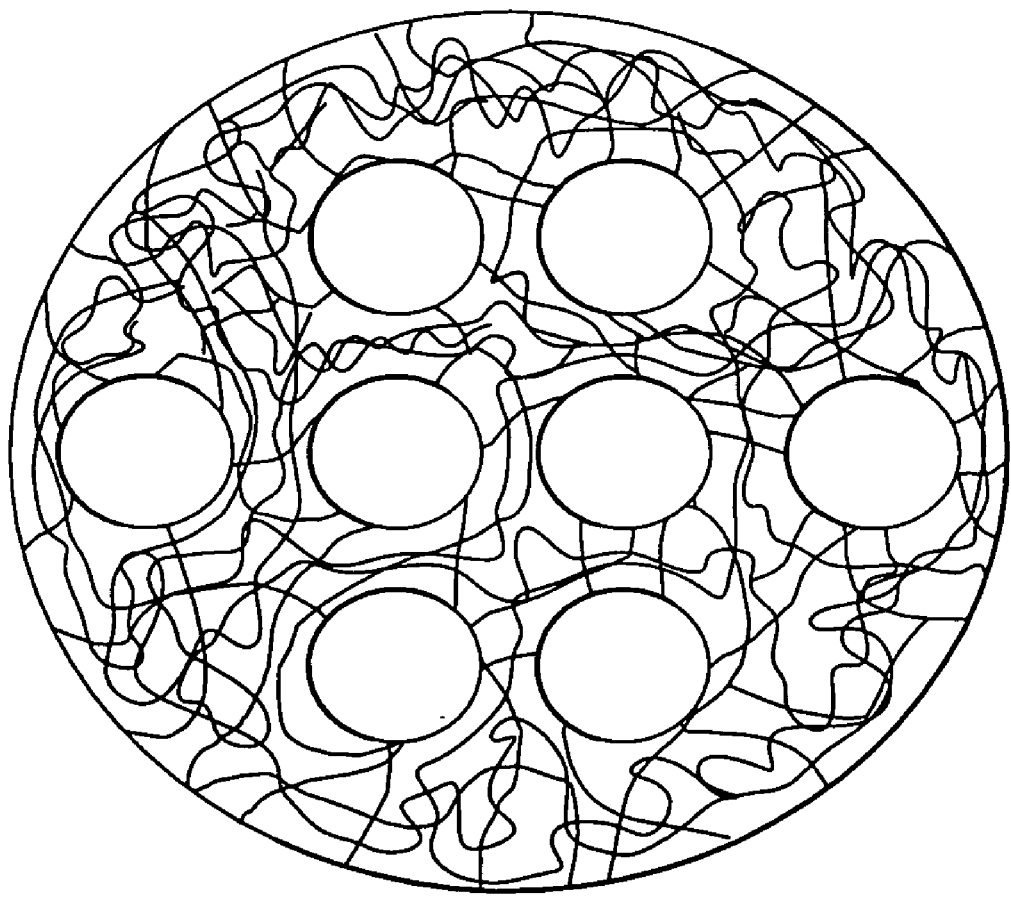

When a photomask similar to the one depicted in FIG. 1A (93% opacity with 0% opacity circles of 500 micrometer diameter spaced 2 mm apart) was used and the liquid phase polymerization formulation containing the degradable crosslinker was exposed to the initiating light for 35 seconds, a patterned hydrogel formed with a thickness of 760 micrometers. A second mask was prepared that consisted of 93% opacity with a 0% opacity rectangle (200 micrometers in width and 4 mm in length). When this mask was used in conjunction with larger Teflon spacers (1.1 mm thick), exposure of the liquid phase polymerization formulation containing the degradable crosslinker to the initiating light for 35 seconds formed a patterned hydogel with a thickness of 1.1 mm.

To confirm that these gels were degradable, the hydrolysis of the ester linkage in the caprolactone segment of the crosslinker was accelerated by placing the gels in a basic solution (2M NaOH). The gels were placed in 37° C. bath overnight, after which time the gels were completely degraded. The basic solution was neutralized to a pH of 7 and the degradation products remained soluble.

EXAMPLE 3

This example describes an exemplary method of the invention for forming photopatterned, porous hydrogels.

A. Materials and Methods

Figure 2A:
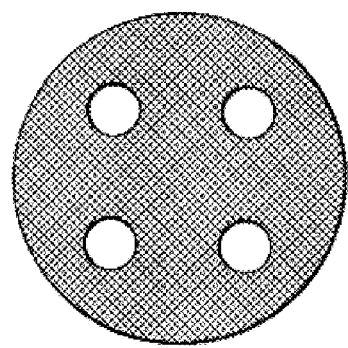
FIGS. 2A–C show a photomask (FIG. 2A) used to create a patterned hydrogel (FIG. 2B) and a patterned, porous hydrogel (FIG. 2C), as described in EXAMPLE 3.

Photomask: Photomasks were generated as described in EXAMPLE 1. The pattern shown in FIG. 2A was drawn with 93% opacity and the regions where open channels were desired were clear (i.e., 0% opacity).

Sphere Templating and Photopolymerization: A microsphere template was fabricated by using sieved linear poly (methyl methacrylate) microspheres with a molecular weight of 25K. The spheres were packed tightly together between two glass slides and a Teflon spacer (760 micrometers thick) and heated to 140° C. for 19 hours to fuse the spheres. The polymerization formulation described in EXAMPLE 1 was poured over the microsphere template and a photomask was placed on top. The sample was exposed to 365 nm light with an incident light intensity of 850 mW/cm$^2$ under the 0% opacity regions of the photomask and 45 mW/cm$^2$ under the 93% opacity regions of the photomask for 30 seconds. The microspheres were removed by repeated washes with 90% acetone/10% water.

Scanning Electron Microscopy: Scanning electron microscopy was performed as described in EXAMPLE 1.

B. Results

Figure 2B:
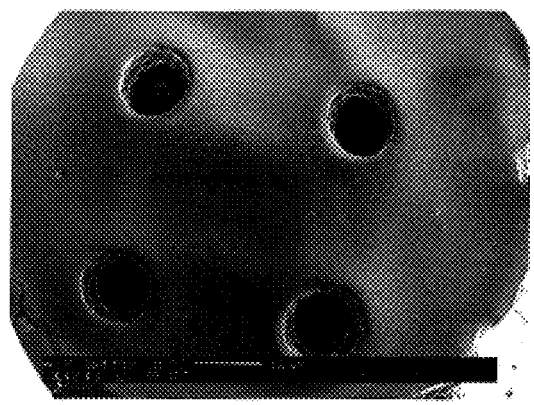
Figure 2C:
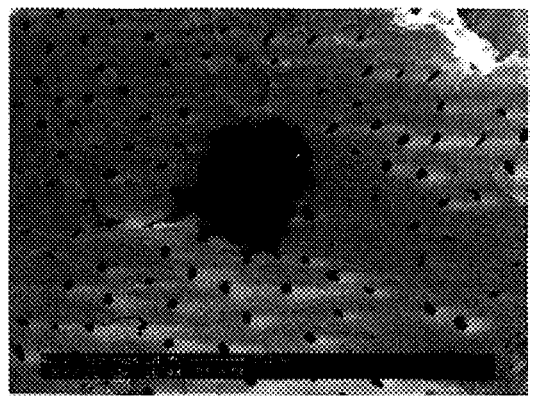

In designing a cell scaffold suitable for cardiac muscle tissue engineering, oxygen transport is critical. Generating open, parallel channels in a porous scaffold is likely to facilitate oxygen transport and enhance cell viability and function throughout the scaffold. A porous and patterned hydrogel scaffold based on poly(2-hydroxyethyl methacrylate) (poly(HEMA) has been successfully formed using a sphere templating method to generate well-defined pores combined with photopolymerization of the hydrogel to create open channels within the hydrogel scaffold, as shown in FIGS. 2B and C. The channels were approximately 500 micrometers spaced 2 mm apart as dictated by the features on the mask. The thickness of the material was 760 micrometers. When the sphere template was introduced into the system, channels were similarly generated (FIG. 2C). The features on the mask were also varied to generate channels with diameters that were about 200, 500, and 1000 micrometers. Thus, the sphere templating method enables facile fabrication of porous photopatterned pHEMA hydrogels with a range of monodisperse pore sizes in one easy step.

EXAMPLE 4

This example describes an exemplary method of the invention for photopatterning degradable, porous hydrogel scaffolds that incorporates cell adhesion proteins.

A. Materials and Methods

Photomask: Photomasks were generated as described in EXAMPLE 1. The pattern shown in FIG. 2A was drawn with 93% opacity and the regions where open channels were desired were clear (i.e., 0% opacity).

Sphere Templating and Photopolymerization: A microsphere template was fabricated as described in EXAMPLE 3. Photopolymerization with a hydrolytically labile crosslinker, poly($\epsilon$-caprolactone)-b-tetraethylene glycol-b-poly($\epsilon$-caprolactone) was performed as described in EXAMPLE 2. Patterned and porous degradable scaffolds were readily obtained. To create a cell adhesive scaffold, collagen type I was immobilized onto the degradable poly (HEMA) scaffolds. In brief, the hydroxyl side groups along the HEMA backbone were reacted with 1,1 carbonyldiimidazole. Collagen type I was then reacted with the CDI-activated HEMA. Elemental spectroscopy for chemical analysis results indicated an increase in elemental N1s composition from 0% in the poly(HEMA) control to 1.6% in the poly(HEMA)-CDI activated scaffold to 7.0% in the poly(HEMA) scaffold immobilized with collagen type I. These results confirm the successful incorporation of collagen type I to poly(HEMA) scaffolds.

Seeding of C2C12 Skeletal Myoblasts: A skeletal myoblast cell line (C2C12, ATCC) was used as a model cell type to examine these pHEMA hydrogels as tissue engineering scaffolds. The pHEMA hydrogels were sterilized in 70% ethanol for several hours and lyophilized overnight. The gels were reacted with CDI and collagen type I as described above. The gels were rinsed in phosphate buffered saline and placed in medium containing serum overnight. One million myoblasts were seeded on to each of the pHEMA scaffolds and cultured for 7 days. After 7 days, the gels were processed under standard histological procedures.

B. Results

To create scaffolds that are better suited for tissue engineering, degradable poly(HEMA) gels were fabricated and cell adhesion proteins were incorporated into the scaffold to promote cell adhesion. C2C12 skeletal myoblasts were seeded onto patterned, porous and degradable pHEMA hydrogels. After 7 days in vitro, histological analysis indicated that the incorporation of collagen type I promoted cell adhesion while little cell presence was observed in the control scaffold without collagen. In the collagen type I scaffold, myoblasts were located throughout the pores and cell spreading was observed.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for forming a photopatterned hydrogel, comprising the step of:

exposing a solution comprising a monomer, a crosslinking agent, and a photoinitiator to a pattern of light comprising a first and a second light intensity for a period of time and under suitable conditions for the first light intensity to induce essentially complete conversion of polymerizable groups on the monomer and the crosslinking agent to form a patterned hydrogel, and for the second light intensity to induce partial conversion of the polymerizable groups on the monomer and the crosslinking agent to form partially polymerized polymers that remain soluble.

2. The method of claim 1, wherein the first light intensity is lower than the second light intensity.

3. The method of claim 1, wherein the monomer is selected from the group consisting of a methacrylates derivative, an acrylate derivative, ethylene, a diene, a styrene, a halogenated olefin, a vinyl ester, an acrylonitrile, an acrylamide, an n-vinyl pyrrolidone, and a mixture thereof.

4. The method of claim 3, wherein the methacrylate derivative is selected from the group consisting of 2-hydroxyethyl methacrylate, methyl methacrylate, methacrylic acid, n-butyl methacrylate, glycidyl methacrylate, n-propyl methacrylate, poly(ethylene glycol)monomethacrylate, and a mixture thereof.

5. The method of claim 3, wherein the acrylate derivative is selected from the group consisting of 2-hydroxyethyl acrylate, 2-methoxyethyl acrylate, acrylic acid, n-butyl acrylate, glycidyl acrylate, n-propyl acrylate, poly(ethylene glycol)monoacrylate, and a mixture thereof.

6. The method of claim 1, wherein the crosslinking agent is selected from the group consisting of tetraethylene glycol dimethacrylate, tetraethylene glycol diacrylate, ethylene glycol dimethacrylate, ethylene glycol diacrylate, dipropylene glycol dimethacrylate, dipropylene glycol diacrylate, poly(ethylene glycol)dimethacrylate, poly(ethylene glycol) diacrylate, bisacrylamide, and a mixture thereof.

7. The method of claim 1, wherein the photoinitiator is selected from the group consisting of 2,2-dimethoxy acetophenone, 1-hydroxycyclohexyl phenyl ketone, 2-methyl-1-[4-(methylthio)phenyl]-2-(4-morpholinyl)-1-propoanone, 2-hydroxy-1-[4-(hydroxyethoxy)phenyl]-2-methyl-1-propanone, and a mixture thereof.

8. The method of claim 1, wherein the photopatterned hydrogel is degradable.

9. The method of claim 8, wherein the crosslinking agent is hydrolytically degradable.

10. The method of claim 9, wherein the hydrolytically degradable crosslinking agent is selected from the group consisting of poly($\epsilon$-caprolactone)-b-tetraethylene glycol-b-poly($\epsilon$-caprolactone) dimethacrylate, poly($\epsilon$-caprolactone)- b-poly(ethylene glycol)-b-poly(ε-caprolactone)dimethacrylate, poly(lactic acid)-b-tetraethylene glycol-b-poly(lactic acid) dimethacrylate, poly(lactic acid)-b-poly(ethylene glycol)-b-poly(lactic acid) dimethacrylate, poly(glycolic acid)-b-tetraethylene glycol-b-poly(glycolic acid)dimethacrylate, poly(glycolic acid)-b-poly(ethylene glycol)-b-poly(glycolic acid)dimethacrylate, poly(ε-caprolactone)-b-tetraethylene glycol-b-poly(ε-caprolactone)diacrylate, poly(ε-caprolactone)-b-poly(ethylene glycol)-b-poly(ε-caprolactone)diacrylate, poly(lactic acid)-b-tetraethylene glycol-b-poly(lactic acid)diacrylate, poly(lactic acid)-b-poly(ethylene glycol)-b-poly(lactic acid)diacrylate, poly(glycolic acid)-b-tetraethylene glycol-b-poly(glycolic acid)diacrylate, poly(glycolic acid)-b-poly(ethylene glycol)-b-poly(glycolic acid) diacrylate, and a mixture thereof.

11. The method of claim 1, wherein the photopatterned hydrogel has a thickness greater than about 25 micrometers.

12. The method of claim 1, wherein the photopatterned hydrogel has a thickness between about 50 micrometers and about 1200 micrometers.

13. A method for forming a photopatterned hydrogel, comprising the step of:
exposing a solution comprising a monomer, a crosslinking agent, and a photoinitiator to a pattern of light comprising a first and a second light intensity for a period of time under suitable conditions to form a photopatterned hydrogel defined by regions of the solution exposed to the first light intensity, wherein the first light intensity is lower than the second light intensity.

14. A method for forming a porous, photopatterned hydrogel, comprising the steps of:
(a) exposing a plurality of porogens in a solution comprising a monomer, a crosslinking agent, and a photoinitiator to a pattern of light comprising a first and a second light intensity for a period of time under suitable conditions for the first light intensity to induce essentially complete conversion of polymerizable groups on the monomer and the crosslinking agent to form a patterned hydrogel, and for the second light intensity to induce partial conversion of polymerizable groups on the monomer and the crosslinking agent to form polymers that remain soluble; and
(b) removing the plurality of porogens to form a porous, photopatterned hydrogel.

15. The method of claim 14, wherein the first light intensity is lower than the second light intensity.

16. The method of claim 14, wherein the monomer is selected from the group consisting of a methacrylates derivative, an acrylate derivative, ethylene, a diene, a styrene, a halogenated olefin, a vinyl ester, an acrylonitrile, an acrylamide, an n-vinyl pyrrolidone, and a mixture thereof.

17. The method of claim 14, wherein the crosslinking agent is selected from the group consisting of tetraethylene glycol dimethacrylate, tetraethylene glycol diacrylate, ethylene glycol dimethacrylate, ethylene glycol diacrylate, dipropylene glycol dimethacrylate, dipropylene glycol diacrylate, poly(ethylene glycol)dimethacrylate, poly(ethylene glycol)diacrylate, bisacrylamide, and a mixture thereof.

18. The method of claim 14, wherein the photoinitiator is selected from the group consisting of 2,2-dimethoxy acetophenone, 1-hydroxycyclohexyl phenyl ketone, 2-methyl-1-[4-(methylthio)phenyl]-2-(4-morpholinyl)-1-propoanone, 2-hydroxy-1-[4-(hydroxyethoxy)phenyl]-2-methyl-1-propanone, and a mixture thereof.

19. The method of claim 14, wherein the porous, photopatterned hydrogel is degradable.

20. The method of claim 19, wherein the crosslinking agent is hydrolytically degradable.

21. The method of claim 20, wherein the hydrolytically degradable crosslinking agent is selected from the group consisting of poly(ε-caprolactone)-b-tetraethylene glycol-b-poly(ε-caprolactone)dimethacrylate, poly(ε-caprolactone)-b-poly(ethylene glycol)-b-poly(ε-caprolactone)dimethacrylate, poly(lactic acid)-b-tetraethylene glycol-b-poly(lactic acid)dimethacrylate, poly(lactic acid)-b-poly(ethylene glycol)-b-poly(lactic acid)dimethacrylate, poly(glycolic acid)-b-tetraethylene glycol-b-poly(glycolic acid)dimethacrylate, poly(glycolic acid)-b-poly(ethylene glycol)-b-poly(glycolic acid)dimethacrylate, poly(ε-caprolactone)-b-tetraethylene glycol-b-poly(ε-caprolactone)diacrylate, poly(ε-caprolactone)-b-poly(ethylene glycol)-b-poly(ε-caprolactone)diacrylate, poly(lactic acid)-b-tetraethylene glycol-b-poly(lactic acid)diacrylate, poly(lactic acid)-b-poly(ethylene glycol)-b-poly(lactic acid) diacrylate, poly(glycolic acid)-b-tetraethylene glycol-b-poly(glycolic acid)diacrylate, poly(glycolic acid)-b-poly(ethylene glycol)-b-poly(glycolic acid) diacrylate, and a mixture thereof.

22. The method of claim 14, wherein the porous, photopatterned hydrogel has a thickness between about 50 micrometers and about 1200 micrometers.

23. A method for forming a porous, photopatterned hydrogel, comprising the steps of:
(a) exposing a plurality of porogens in a solution comprising a monomer, a crosslinking agent, and a photoinitiator to a pattern of light comprising a first and a second light intensity for a period of time under suitable conditions to form a photopatterned hydrogel defined by regions of the solution exposed to the first light intensity, wherein the first light intensity is lower than the second light intensity; and
(b) removing the plurality of porogens to form a porous, photopatterned hydrogel.

* * * * *

UNITED STATES PATENT AND TRADEMARK OFFICE
CERTIFICATE OF CORRECTION

PATENT NO.        : 7,192,693 B2
APPLICATION NO. : 11/067480
DATED             : March 20, 2007
INVENTOR(S)       : S. J. Bryant et al.

Page 1 of 1

It is certified that error appears in the above-identified patent and that said Letters Patent is hereby corrected as shown below:

| COLUMN | LINE | ERROR |
|---|---|---|
| 1 | 15-20 | delete the paragraph beginning "The U.S. Government..." and ending "of Health." and substitute therefor --This invention was made with U.S. Government support under grant numbers R24 HL64387 and F32 HL74619-01 awarded by National Institutes of Health. The U.S. Government has certain rights in the invention.-- |

Signed and Sealed this

Eighteenth Day of March, 2008

JON W. DUDAS
*Director of the United States Patent and Trademark Office*